(12) United States Patent
Hohberg et al.

(10) Patent No.: US 7,153,922 B2
(45) Date of Patent: Dec. 26, 2006

(54) ORGANOSILICON COMPOUNDS HAVING POLYOXYALKYLENE RADICALS

(75) Inventors: Thomas Hohberg, Burghausen (DE); Christian Ochs, Burghausen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 10/831,042

(22) Filed: Apr. 23, 2004

(65) Prior Publication Data

US 2004/0225099 A1    Nov. 11, 2004

(30) Foreign Application Priority Data

May 8, 2003    (DE) ................ 103 20 631

(51) Int. Cl.
*C08G 77/26* (2006.01)
(52) U.S. Cl. ............... 528/28; 528/27; 528/38; 252/8.61; 252/8.62; 252/8.63
(58) Field of Classification Search ............... 528/27, 528/38; 252/8.61, 8.62, 8.63; 424/70.122
See application file for complete search history.

(56) References Cited

U.S. PATENT DOCUMENTS

| | | | | |
|---|---|---|---|---|
| 4,680,366 | A * | 7/1987 | Tanaka et al. | 528/27 |
| 5,981,681 | A * | 11/1999 | Czech | 528/27 |
| 6,030,675 | A | 2/2000 | Schroeder et al. | |
| 6,072,017 | A * | 6/2000 | Blizzard et al. | 528/26 |
| 6,313,256 | B1 | 11/2001 | O'Lenick, Jr. | |
| 6,482,969 | B1 * | 11/2002 | Helmrick et al. | 556/420 |

2004/0048996 A1   3/2004   Lange et al.

FOREIGN PATENT DOCUMENTS

| | | |
|---|---|---|
| DE | 3 307 473 | 9/1984 |
| DE | 4 007 597 | 9/1991 |
| DE | 19 817 776 | 10/1999 |
| EP | 1 000 959 | 5/2000 |
| WO | WO 02/10257 | 2/2002 |
| WO | WO 02/10257 A1 | 2/2002 |
| WO | WO 03/035721 A1 | 5/2003 |

OTHER PUBLICATIONS

Derwent Abstract corresponding to DE 4 007 597 [AN 1991-274837].
Derwent Abstract corresponding to DE 19 817 776 [AN 1999-602368].
Derwent Abstract corresponding to DE 3 307 473 [AN 1984-226115].
Patent Abstract of Japan Corresponding to JP 2002308991—Oct. 23, 2002.
Derwent Abstract corresponding to EP 1 000 959 [AN 2000-352304].
Derwent Abstract corresponding to WO 02/10257 [AN 2002-382420].

* cited by examiner

*Primary Examiner*—Marc S. Zimmer
(74) *Attorney, Agent, or Firm*—Brooks Kushman P.C.

(57) ABSTRACT

Organosilicon compounds contain both cationic quat groups and polyoxyalkylene polyether groups prepared by an efficient process which can utilize commercially available starting materials. The polyether groups are not linked to siloxane moieties by quat linking groups, but rather by amine or ammonium groups. The polyester groups may also serve as linking groups between organosilicon moieties.

5 Claims, No Drawings

ORGANOSILICON COMPOUNDS HAVING POLYOXYALKYLENE RADICALS

BACKGROUND OF THE INVENTION

1. Field of the Invention

This invention relates to organosilicon compounds wherein cationic quat groups and polyether groups are attached to a siloxane body via an amino or ammonium group, and to processes for preparing them.

2. Background Art

Ternary polysiloxane systems consisting of polysiloxane units, polyether groups and cationic quat groups are of particular interest for use as textile softeners. However, the syntheses described are exclusively very time-intensive, multi-step processes, since the reactants used are often not available in industry and have to be explicitly prepared. The associated poor space-time yields render existing synthetic processes uneconomical and impracticable.

Known ternary polysiloxane systems of the kind mentioned above can be divided into 4 different classes: A) strictly comb type modified siloxane polymers wherein a polyether group acts as a linking member between the siloxane scaffold and the cationic quat group, or vice versa, i.e., wherein the cationic quat group acts as a linking member between the siloxane scaffold and the polyether group, are described for example in U.S. Pat. No. 6,030,675; B) linear siloxane copolymers having terminal cationic quat groups and polyether groups, wherein the polyether group may also be a linking member to a further siloxane block having a terminal quat group, are described for example in EP 1000959 A; C) polymers wherein the cationic quat groups constitute a bridging element between 2 siloxane blocks of the polymer, wherein additional polyether groups may be present as 2-valent linking members in the polymer main chain, or the siloxane scaffold or the cationic quat group is comb type polyether-modified, are described for example in WO 02/10257 A1; D) polysiloxanes which have been terminally and/or laterally modified with mutually independent polyether groups and cationic quat groups are described for example in U.S. Pat. No. 6,313,256 A.

SUMMARY OF THE INVENTION

The subject invention pertains to organosilicon compounds containing both cationic quat groups and polyoxyalkylene polyether groups prepared by an efficient process which can utilize commercially available starting materials. The polyether groups are not linked to siloxane moieties by quat linking groups, but rather by amine or ammonium groups. The polyether groups may also serve as linking groups between organosilicon moieties.

DETAILED DESCRIPTION OF THE PREFERRED EMBODIMENT(S)

The invention provides copolymers (Q) of the general formula (I)

$$A-B-(D-B)_o-A \quad (I),$$

where
A is an $-R^1$ or $-OR^1$ radical or a monovalent radical of the general formula (II),

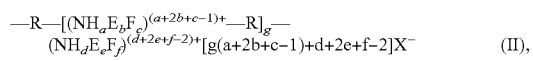

(II)

$R^1$ is a hydrogen atom or a monovalent hydrocarbyl radical having 1 to 100 carbon atoms that may optionally be interrupted or substituted by the atoms N, O, P, B, Si, S, or contain $-C(O)-$, $-C(O)O-$, $-C(O)NR^9-$, $-NR^9-$, $-O-$, $-S-$, $=N-$, $\equiv N$ units, or be substituted by $-NR^9-$, $-OH$, or $-SH$ groups, R is a divalent hydrocarbyl radical having 1 to 50 carbon atoms that may optionally be interrupted or substituted by the atoms N, O, P, B, Si, S, or contain $-C(O)-$, $-C(O)O-$, $-C(O)NR^9-$, $-NR^9-$, $-O-$, $-S-$, $=N-$ units, $R^9$ is a hydrogen atom or a monovalent hydrocarbyl radical having 1 to 18 carbon atoms that may optionally be interrupted by the atoms N, O, P, B, Si, S, or substituted by $-OH$, or $-SH$ groups, a, b and c are integers from 0 to 2 subject to the condition that the sum total of a+b+c is 1 or 2, d, e and f are integers from 0 to 3 subject to the condition that the sum total of d+e+f is 2 or 3, g is an integer from 0 to 10, E is a radical of the general formula (III)

(III), $R^2$ is a divalent hydrocarbyl radical having 1 to 10 carbon atoms that may optionally be interrupted or substituted by the atoms N, O, P, B, Si, S, or contain $-C(O)-$, $-C(O)O-$, $-C(O)NR^9-$, $-NR^9-$, $-O-$, $-S-$, $=N-$, $\equiv N$ units, or be substituted by $-NR^9-$, $-OH$, $-SH$ groups, $R^3$ is a monovalent hydrocarbyl radical having 1 to 20 carbon atoms that may optionally be interrupted or substituted by the atoms N, O, P, B, Si, S or contain $-C(O)-$, $-C(O)O-$, $-C(O)NR^9-$, $-NR^9-$, $-O-$, $-S-$, $=N-$, $\equiv N$ units, or be substituted by $-NR^9-$, $-OH$, $-SH$ groups, $X^-$ is an organic or inorganic anion, F is a radical of the general formulae (IV) or (V)

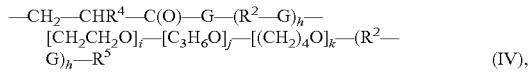

(IV),

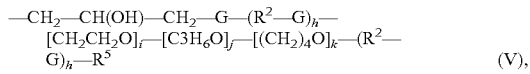

(V), $R^4$ is a hydrogen atom or methyl radical, $R^5$ is a hydrogen atom, a monovalent branched or unbranched hydrocarbyl radical having 1 to 10 carbon atoms or a unit selected from the group consisting of $CH_2=CR^4-C(O)-$, $(R^1)_2N-CH_2-CHR^4-C(O)-$, $R^4-CH_2-C(O)-$, $HO-CH_2-CH(OH)-CH_2-$ and

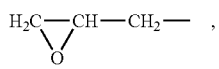,

G is a divalent group $-O-$ or $-NR^9-$, h is 0 or 1, i, j and k are each an integer from 0 to 200, B is a divalent radical constructed from units which are selected from the general formulae (VIa), (VIb), (VIc), (VId) and A

 (VIa),

 (VIb),

 (VIc),

 (VId), $R^6$ is a hydrogen atom, $-OR^1$, or a monovalent alkyl radical having 1 to 200 carbon atoms which may be substituted by halogen atoms, carboxyl groups, epoxy groups, hydroxyl groups or polyether groups and may optionally be interrupted by the units $-C(O)-$, $-C(O)O-$, $-C(O)NR^9-$, $-NR^9-$, $-O-$, $-S-$, $R^7$ is a monovalent radical of the general formula (II), l and m are an integer from 0 to 5000, p is an integer from 0 to 500, D is a divalent radical of the general formula (VIII), $$-\{[R-(NH_aE_bF_c)]_n-J-[(NH_aE_bF_c)-R]_n\}^{[2n(a+2b+c)-4]+}[2n(a+2b+c)-4]X^- \quad (VIII),$$

n is an integer from 1 to 10,

J is a divalent radical of the general formulae (IX) or (X),

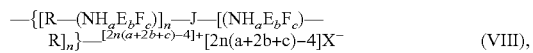

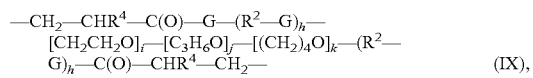

o is an integer $\geq 0$, with the proviso that the copolymers of the general formula (I) contain at least one E radical and one F radical.

In contrast to known structures, the cationic quat group and the polyether group are bonded to the siloxane body via an amino or ammonium group in the copolymers (Q). The quat group does not act as a bridge, whereas the polyether radical can function as a linking member between 2 aminosiloxane bodies.

The copolymers (Q) are simple to construct in a one-pot process. The syntheses proceed almost quantitatively and because of good space-time yields, are more economical than prior processes leading to other structures. In addition, all raw materials are commercially available in large amounts and do not require additional cost and inconvenience for synthesis. The resulting copolymers (Q) can be rendered water soluble or self-emulsifying (so-called "self-emulsifying systems"), depending on the stoichiometry chosen, i.e., requiring no further auxiliaries for emulsification. The copolymers (Q) can be used for treating textile sheet materials, textile fibers and leather, as additives in coatings and paints, as ingredients in cosmetic formulations and as surface-active agents. They have, in particular, outstanding properties when used as textile softeners properties, which are superior to those of ordinary amino glycol oils.

The copolymers (Q) are linear or branched aminopolysiloxanes whose α, ω and/or lateral amino groups have been modified not only with polyether groups but also with cationic quat groups. The amino groups may optionally be present as quaternary ammonium groups. The number average molecular weight $M_n$ of the copolymers (Q) is preferably at least 500 g/mol, more preferably at least 1000 g/mol, preferably at most 1,000,000 g/mol, and more preferably at most 500,000 g/mol. The viscosity of the copolymers (Q) is preferably in the range from minimally 10 mm²/s, more preferably minimally 15 mm²/s, to solid at 25° C.

The amine number of the copolymers (Q) is preferably at least 0.001, more preferably at least 0.01, and preferably at most 9, more preferably at most 6. The amine number identifies the number of ml of 1 Normal HCl which are necessary to neutralize 1 g of copolymer.

In preferable copolymers, a, b and c are 0 or 1; the sum total of a+b+c is 1; d, e and f are 0, 1 or 2; the sum total of d+e+f is 2 and the sum total of a+b+c+d+e+f is $\leq 5$, especially 3 or 4; g is at most 5, more preferably, 0 or 1; h is 0; i, j and k are each at most 100 and more preferably at most 50; l and m are at most 1000 and more preferably at most 500; p is at most 100 and more preferably at most 20; n is at most 5, more preferably, 1 or 2, most preferably 1; and o is at most 1000 and more preferably at most 100.

Preferably, R is a divalent hydrocarbyl radical having 1 to 10 carbon atoms which may optionally be interrupted by N and/or O atoms. R is more preferably a radical independently selected from the formulae $-CH_2-$, $-(CH_2)_2-$, $-(CH_2)_3-$, $-(CH_2)_2-NH-(CH_2)_3-$, and most preferably a radical from the formulae $-(CH_2)-$, $-(CH_2)_2-$ and $-(CH_2)_3-$.

Preferably, $R^1$ is a hydrogen atom, a saturated or unsaturated alkyl radical having 1 to 10 carbon atoms, or a radical of the formulae $-C(O)H$, $-C(O)CH_3$, $-C(O)CH_2-CH_3$ and $-CH_2-CH_2-C(O)-O-CH_2-CH_3$. Particular preference is given to hydrogen, methyl, ethyl, propyl, cyclohexyl and acetyl.

Preferably, $R^2$ is independently selected from an uninterrupted divalent hydrocarbyl radical having 1 to 8 carbon atoms and the radical $-CH_2-CH(OH)-CH_2-$. Preferred examples of $R^2$ are linear or branched alkylene radicals such as the ethylene, propylene, butylene radical, arylene radicals such as the phenylene radical and the radical $-CH_2-CH(OH)-CH_2-$.

Preferably, $R^3$ is an uninterrupted monovalent alkyl radical. Particular preference is given to methyl, ethyl, propyl, butyl, cyclohexyl, dodecyl and octadecyl.

Preferably, $R^4$ is a hydrogen atom.

Preferably, $R^5$ is a hydrogen atom, a saturated or unsaturated alkyl radical having 1 to 5 carbon atoms or one of the radicals

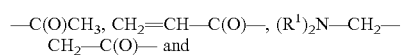

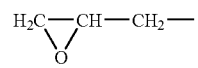

Particular preference is given to hydrogen, methyl, ethyl, butyl, acetyl, acryloyl and

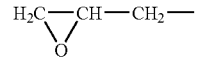

Examples of $R^6$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals; hexyl radicals such as the n-hexyl radical; heptyl radicals such as the n-heptyl radical; octyl radicals such as the n-octyl radical and isooctyl radicals such as the 2,2,4-trimethylpentyl radical; nonyl radicals such as the n-nonyl radicals; decyl radicals such as the n-decyl radical; dodecyl radicals such as the n-dodecyl radical; octadecyl radicals such as the n-octadecyl radical; cycloalkyl radicals such as the cyclopentyl, cyclohexyl, cycloheptyl and methylcyclohexyl radicals; alkenyl radicals such as the vinyl, allyl, 3-butenyl, 5-hexenyl, 1-propenyl and 1-pentenyl radicals; alkynyl radicals such as the ethynyl, propargyl and 1-propynyl radicals; aryl radicals such as the phenyl, naphthyl, anthryl and phenanthryl radicals; alkaryl radicals such as the o-, m-, p-tolyl radicals, xylyl radicals and ethylphenyl radicals; and aralkyl radicals such as the benzyl, phenylethyl and phenylnonyl radicals, or the methoxy or ethoxy radicals.

Examples of substituted $R^6$ radicals are haloalkyl radicals such as 3,3,3-trifluoro-n-propyl radical, 2,2,2,2',2',2'-hexafluoroisopropyl radical, and heptafluoroisopropyl radical, and haloaryl radicals such as o-, m- and p-chlorophenyl radicals, or alkyl radicals substituted by carboxyl, epoxy, hydroxyl or polyether groups. Preferably, $R^6$ is a hydrogen atom or a monovalent alkyl radical having 1 to 10 carbon atoms. Methyl is particularly preferred.

Examples of the radical $R^7$ are

—$CH_2$—{N[—$CH_2$—CH(OH)—$CH_2$—$NMe_3$]F}$^+$ Cl$^-$,
—$CH_2$—{N[—$CH_2$—CH(OH)—$CH_2$—$NMe_3$]$_2$F}$^{3+}$ 3Cl$^-$,
—$(CH_2)_3$—{N[—$CH_2$—CH(OH)—$CH_2$—$NMe_3$]F}$^+$ Cl$^-$,
—$(CH_2)_3$—{N[—$CH_2$—CH(OH)—$CH_2$—$NMe_3$]$_2$F}$^{3+}$ 3Cl$^-$,
—$(CH_2)_3$—NH—$(CH_2)_2$—{N[—$CH_2$—CH(OH)—$CH_2$—$NMe_3$]F}$^{3+}$ Cl$^-$,
—$(CH_2)_3$—{N[—$CH_2$—CH(OH)—$CH_2$—$NMe_3$]—$(CH2)_2$—NHF}$^+$ Cl$^-$,
—$(CH_2)_3$—NF—$(CH_2)_2$—{NH[—$CH_2$—CH(OH)—$CH_2$—$NMe_3$]}$^+$ Cl$^-$,
—$(CH_2)_3$—{N[—$CH_2$—CH(OH)—$CH_2$—$NMe_3$]—$(CH_2)_2$—$NF_2$}$^+$ Cl$^-$,
—$(CH_2)_3$—NF—$(CH_2)_2$—{N[—$CH_2$—CH(OH)—$CH_2$—$NMe_3$]F}$^+$ Cl$^-$,
—$(CH_2)_3$—{N[—$CH_2$—CH(OH)—$CH_2$—$NMe_3$]—$(CH_2)_2$—N[—$CH_2$—CH(OH)—$CH_2$—$NMe_3$]F}$^{2+}$ 2Cl$^-$,
—$(CH_2)_3$—NF—$(CH_2)_2$—{N[—$CH_2$—CH(OH)—$CH_2$—$NMe_3$]$_2$}$^{2+}$ 2Cl$^-$,
—$(CH_2)_3$—{N[—$CH_2$—CH(OH)—$CH_2$—$NMe_3$]$_2$—$(CH_2)_2$—$NF_2$}$^{3+}$ 3Cl$^-$,
—$(CH_2)_3$—{N[—$CH_2$—CH(OH)—$CH_2$—$NMe_3$]F—$(CH_2)_2$—N[—$CH_2$—CH(OH)—$CH_2$—$NMe_3$]F}$^{3+}$ 3Cl$^-$,
—$(CH_2)_3$—{N[—$CH_2$—CH(OH)—$CH_2$—$NMe_3$]—$(CH_2)_2$—N[—$CH_2$—CH(OH)—$CH_2$—$NMe_3$]$F_2$}$^{3+}$ 3Cl$^-$,
—$(CH_2)_3$—NF—$(CH_2)_2$—{N[—$CH_2$—CH(OH)—$CH_2$—$NMe_3$]$_2$F}$^{3+}$ 3Cl$^-$,
—$(CH_2)_3$—NF—$(CH_2)_2$—N[—$CH_2$—CH(OH)—$CH_2$—$NMe_3$]$_3$}$^{4+}$ 4Cl$^-$,
—$(CH_2)_3$—{N[—$CH_2$—CH(OH)—$CH_2$—$NMe_3$]—$(CH_2)_2$—N[—$CH_2$—CH(OH)—$CH_2$—$NMe_3$]$_2$F}$^{4+}$ 4Cl$^-$,
—$(CH_2)_3$—{N[—$CH_2$—CH(OH)—$CH_2$—$NMe_3$]$_2$—$(CH_2)_2$—N[—$CH_2$—CH(OH)—$CH_2$—$NMe_3$]F}$^{4+}$ 4Cl$^-$,
—$(CH_2)_3$—{N[—$CH_2$—CH(OH)—$CH_2$—$NMe_3$]F—$(CH_2)_2$—N[—$CH_2$—CH(OH)—$CH_2$—$NMe_3$]$_2$}$^{4+}$ 4Cl$^-$, where Me is methyl, and permutation of the examples mentioned for F results in a multiplicity of further, analogous examples. Some illustrative examples of $R^7$ will now be exemplarily recited to demonstrate the range of the copolymers (Q). (Me=methyl):

—$CH_2$—{N[—$CH_2$—CH(OH)—$CH_2$—$NMe_3$][—$CH_2$—CH(OH)—$CH_2$—O—$(C_2H_4O)_5$—$C_4H_9$]}$^+$ Cl$^-$,
—$CH_2$—{N[—$CH_2$—CH(OH)—$CH_2$—$NMe_3$][—$CH_2$—CH(OH)—$CH_2$—O—$(C_3H_6O)_{20}$—$(C_2H_4O)_{20}$—$C_4H_9$]}$^+$ Cl$^-$,
—$CH_2$—{N[—$CH_2$—CH(OH)—$CH_2$—$NMe_3$][—$CH_2$—$CH_2$—C(O)—O—$(C_2H_4O)_5$—H]}$^+$ Cl$^-$,
—$CH_2$—{N[—$CH_2$—CH(OH)—$CH_2$—$NMe_3$][—$CH_2$—$CH_2$—C(O)—O—$(C_3H_6O)_{16}$—$CH_3$]}$^+$ Cl$^-$,
—$CH_2$—{N[—$CH_2$—CH(OH)—$CH_2$—NMe][—$CH_2$—$CH_2$—C(O)—O—$(C_3H_6O)_{20}$—$C_2H_4O)_{20}$—C(O)—CH=$CH_2$]}$^+$ Cl$^-$,
—$(CH_2)_3$—{N[—$CH_2$—CH(OH)—$CH_2$—$NMe_3$][—$CH_2$—CH(OH)—$CH_2$—O—$(C_2H_4O)_5$—$CH_3$]}$^+$ Cl$^-$,
—$(CH_2)_3$—{N[—$CH_2$—CH(OH)—$CH_2$—$NMe_3$][—$CH_2$—CH(OH)—$CH_2$—O—$(C_3H_6O)_{20}$—$C_3H_5O$]}$^+$ Cl$^-$,
—$(CH_2)_3$—{N[—$CH_2$—CH(OH)—$CH_2$—$NMe_3$][—$CH_2$—CH(OH)—$CH_2$—O—$(C_2H_4O)_6$—$CH_2CH(OH)CH_2OH$]}$^+$ Cl$^-$,
—$(CH_2)_3$—{N[—$CH_2$—CH(OH)—$CH_2$—$NMe_3$][—$CH_2$—$CH_2$—C(O)—O—$(C_2H_4O)_{25}$—$C(O)CH_3$]}$^+$ Cl$^-$,
—$(CH_2)_3$—{N[—$CH_2$—CH(OH)—$CH_2$—$NMe_3$][—$CH_2$—$CH_2$—C(O)—O—$(C_3H_6O)_{16}$—$CH_3$]}$^+$ Cl$^-$,
—$(CH_2)_3$—{N[—$CH_2$—CH(OH)—$CH_2$—$NMe_3$][—$CH_2$—$CH_2$—C(O)—O—$(C_3H_6O)_{20}$—$(C_2H_4O)_{20}$—C(O)—$CH_2CH_2$—$NEt_2$]}$^+$ Cl$^-$,
—$(CH_2)_3$—NH—$(CH_2)_2$—{N[—$CH_2$—CH(OH)—$CH_2$—$NMe_3$][—$CH_2$—CH(OH)—$CH_2$—O—$(C_2H_4O)_5$—$C_4H_9$]}$^+$ Cl$^-$,
—$(CH_2)_3$—NH—$(CH_2)_2$—{N[—$CH_2$—CH(OH)—$CH_2$—$NMe_3$][—$CH_2$—CH(OH)—$CH_2$—O—$(C_2H_4O)_{22}$—$(C_3H_6O)_{19}$—$C_4H_9$]}$^+$ Cl$^-$,
—$(CH_2)_3$—{N[—$CH_2$—CH(OH)—$CH_2$—$NMe_3$]—$(CH_2)_2$—N[—$CH_2$—CH(OH)—$CH_2$—O—$(C_2H_4O)_{11}$—$C_4H_9$]H}$^+$ Cl$^-$,
—$(CH_2)_3$—N[—$CH_2$—CH(OH)—$CH_2$—O—$(C_2H_4O)_{20}$—$C_4H_9$]—$(CH_2)_2$—{NH[—$CH_2$—CH(OH)—$CH_2$—NMe]}$^+$ Cl$^-$,
—$(CH)_3$—NH—$(CH)_2$—{N[—$CH_2$—CH(OH)—$CH_2$—$NMe_3$][—$CH_2$—$CH_2$—C(O)—O—$(C_3H_{60})_{16}$—$CH_3$]}$^+$ Cl$^-$,
—$(CH)_3$—NH—$(CH)_2$—{N[—$CH_2$—CH(OH)—$CH_2$—$NMe_3$][—$CH_2$—CH(OH)—$CH_2$—O—$(C_3H_6O)_2$—H]}$^+$ Cl$^-$,
—$(CH_2)_3$—{N[—$CH_2$—CH(OH)—$CH_2$—$NMe_3$]—$(CH_2)_2$—N[—$CH_2$—$CH_2$—C(O)—O—$(C_2H_4O)_{35}$—C(O)—CH=$CH_2$]H}$^+$ Cl$^-$,
—$(CH_2)_3$—N[—$CH_2$—CH(OH)—$CH_2$—O—$(C_2H_4O)_4$—$C_4H_9$]—$(CH_2)_2$—{N [—$CH_2$—CH(OH)—$CH_2$—$NMe_3$][—$CH_2$—CH(OH)—$CH_2$—O—$(C_2H_4O)_{22}$—$(C_3H_6O)_{19}$—$C_4H_9$]}Cl$^-$,
—$(CH_2)_3$—{N[—$CH_2$—CH(OH)—$CH_2$—$NMe_3$]—$(CH_2)_2$—N[—$CH_2$—CH(OH)—$CH_2$—$NMe_3$][—$CH_2$—CH(OH)—$CH_2$—O—$(C_2H_4O)_{24}$—$CH_3$]}$^{2+}$ 2Cl$^-$,
—$(CH_2)_3$—{N[—$CH_2$—CH(OH)—$CH_2$—$NMe_3$][—$CH_2$—CH(OH)—$CH_2$—$(C_2H_4O)_5$—$C_4H_9$]—$(CH_2)_2$—N[—$CH_2$—CH(OH)—$CH_2$—$NMe_3$][—$CH_2$—$CH_2$—C(O)—O—$(C_2H_4O)_{15}$—$(C_3H_6O)_5$—$CH_3$]}$^{3+}$ 3Cl$^-$,
—$(CH_2)_3$—{N [—$CH_2$—CH(OH)—$CH_2$—$NMe_3$]—$(CH_2)_2$—N[—$CH_2$—CH(OH)—$CH_2$—$NMe_3$][—$CH_2$—CH(OH)—$CH_2$—O—$(C_2H_4O)_{11}$—$C_4H_9$][—$CH_2$—$CH_2$—C(O)—O—$(C_2H_4O)_{16}$—$CH_3$]})$^{3+}$ 3Cl$^-$,
—$(CH_2)_3${N[—$CH_2$—CH(OH)—$CH_2$—$NMe_3$]—$(CH_2)_2$—N[—$CH_2$—CH(OH)—$CH_2$—$NMe_3$]$_2$[—$CH_2$—CH(OH)—$CH_2$—O—$(C_2H_4O)_{22}$—$(C_3H_6O)_{19}$—$C_4H_9$]}$^{4+}$ 4Cl$^-$,
—$(CH_2)_3$—{N[—$CH_2$—$CH_2$—C(O)—O—$(C_2H_4O)_{35}$—$CH_3$]—$(CH_2)_2$—N[—$CH_2$—CH(OH)—$CH_2$—$NMe_3$]$_2$[—$CH_2$—CH(OH)—$CH_2$—$(C_2H_4O)_4$—$C_4H_9$]}$^{4+}$ 4Cl$^-$.

Examples of A include hydrogen, the —OH group and also the radicals mentioned for $R^6$ and $R^7$.

Examples of B include
—$SiMe_2$—O—$SiMe_2$—,
—$(SiMe_2O)_{13}$—$SiMe_2$—,
—$(SiMe_2O)_{55}$—$SiMe_2$—,
—$(SiMe_2O)_{105}$—$SiMe_2$—,
—$(SiMe_2O)_{200}$—$SiMe_2$—,
—$SiMe_2O$—$SiMeR^7O$—$SiMe_2O$—, —(SiMe$_2$O)$_{70}$(SiMeR$^7$O)$_1$—SiMe$_2$—,
—(SiMe$_2$O)$_{105}$(SiMeR$^7$O)$_{20}$—SiMe$_2$—,
—(SiMe$_2$O)$_{195}$(SiMeR$^7$O)$_{15}$—SiMe$_2$—,
—(SiMe$_2$O)$_{230}$(SiMeR$^7$O)$_6$—SiMe$_2$—,
—(SiMe$_2$O)$_{108}$(SiMeR$^7$O)$_2$—SiMe$_2$—,
—(SiMe$_2$O)$_{139}$(SiMeR$^7$O)$_1$—SiMe$_2$—,
—(SiMe$_2$O)$_9$—SiMe$_3$,
—(SiMe$_2$O)$_{59}$—SiMe$_3$,
—(SiMe$_2$O)$_{99}$—SiMe$_3$,
—(SiMe$_2$O)$_{13}$—SiMe$_2$—OCH$_3$,
—(SiMe$_2$O)$_{14}$—SiMe$_2$—OC$_2$H$_4$,
—(SiMe$_2$O)$_{44}$—SiMe$_2$—OC$_3$H$_7$,
—(SiMe$_2$O)$_{22}$—SiMe$_2$—OC$_4$H$_9$, and
—(SiMe$_2$O)$_{35}$—SiMe$_2$—OC$_4$H$_9$.

Examples of D include
—{CH$_2$—N[—CH$_2$—CH(OH)—CH$_2$—NMe$_3$]—J—N[—CH$_2$—CH(OH)—CH$_2$—NMe$_3$]—CH$_2$}—$^{2+}$ 2Cl$^-$,
—{CH$_2$—NH—J—N[—CH$_2$—CH(OH)—CH$_2$—NMe$_3$]—CH$_2$}—$^+$ Cl$^-$,
—{CH$_2$—N[—CH$_2$—CH(OH)—CH$_2$—NMe$_3$]—J—NF—CH$_2$}—$^+$ Cl$^-$,
—{CH$_2$—NH—J—NF—CH$_2$}—,
—{CH$_2$—NF—J—NF—CH$_2$}—,
—{(CH)$_3$—N[—CH$_2$—CH(OH)—CH$_2$—NMe$_3$]—J—N[—CH$_2$—CH(OH)—CH$_2$—NMe$_3$]—(CH$_2$)$_3$}—$^{2+}$ 2Cl$^-$,
—{(CH$_2$)$_3$—NH—J—N[—CH$_2$—CH(OH)—CH$_2$—NMe$_3$]—(CH$_2$)$_3$}—$^+$ Cl$^-$,
—{(CH$_2$)$_3$—N[—CH$_2$—CH(OH)—CH$_2$—NMe$_3$]—J—NF—(CH$_2$)$_3$}—$^+$ Cl$^-$,
—{(CH$_2$)$_3$—NH—J—NF—(CH$_2$)$_3$}—,
—{(CH$_2$)$_3$—NF—J—NF—(CH$_2$)$_3$}—,
—{CH$_2$—N[—CH$_2$—CH(OH)—CH$_2$—NMe$_3$]—J—N[—CH$_2$—CH(OH)—CH$_2$—NMe$_3$]—(CH$_2$)$_3$}—$^{2+}$ 2Cl$^-$,
—{CH$_2$—N[—CH$_2$—CH(OH)—CH$_2$—NMe$_3$]—J—NH—(CH$_2$)$_3$}—$^{2+}$ 2Cl$^-$,
—{CH$_2$—NH—J—N[—CH$_2$—CH(OH)—CH$_2$—NMe$_3$]—(CH$_2$)$_3$}—$^{2+}$ 2Cl$^-$,
—{CH$_2$—N[—CH$_2$—CH(OH)—CH$_2$—NMe$_3$]—J—NF—(CH$_2$)$_3$}—$^{2+}$ 2Cl$^-$,
—{CH$_2$—NF—J—N[—CH$_2$—CH(OH)—CH$_2$—NMe$_3$]—(CH$_2$)$_3$}—$^{2+}$ 2Cl$^-$,
—{CH$_2$—NF—J—NF—(CH$_2$)$_3$}—,
—{CH$_2$—NF—J—NH—(CH$_2$)$_3$}—,
—{CH$_2$—NH—J—NF—(CH$_2$)$_3$}—, where Me represents methyl, and permutation of the cited examples with the radicals F and J results in a multiplicity of further illustrative structures.

Examples of E units include
—CH$_2$—CH(OH)—CH$_2$—NMe$_3$$^+$ Cl$^-$, —CH$_2$—CH(OH)—CH$_2$—NMe$_2$Cl$_{12}$H$_{25}$$^+$ Cl$^-$ and
—CH$_2$—CH(OH)—CH$_2$—NMe$_2$Cl$_{18}$H$_{37}$$^+$ Cl$^-$.

Examples of F units are
—CH$_2$—CH$_2$—C(O)—O—(C$_2$H$_4$O)$_6$—H,
—CH$_2$—CH$_2$—C(O)—O—(C$_2$H$_4$O)$_6$—CH$_3$,
—CH$_2$—CH$_2$—C(O)—O—(C$_2$H$_4$O)$_6$—C(O)—CH=CH$_2$,
—CH$_2$—CH$_2$—C(O)—O—(C$_2$H$_4$O)$_6$—C(O)—CH$_2$—CH$_2$—NEt$_2$,
—CH$_2$—CH$_2$—C(O)—O—(C$_2$H$_4$O)$_6$—C(O)—CH$_2$—CH$_2$—N(CH$_2$CH$_2$OH)$_2$,
—CH$_2$—CH$_2$—C(O)—O—(C$_2$H$_4$O)$_6$—C(O)CH$_3$,
—CH$_2$—CH$_2$—C(O)—O—(C$_2$H$_4$O)$_{14}$—H,
—CH$_2$—CH$_2$—C(O)—O—(C$_2$H$_4$O)$_{14}$—CH$_3$,
—CH$_2$—CH$_2$—C(O)—O—(C$_2$H$_4$O)$_{14}$—C(O)—CH=CH$_2$,
—CH$_2$—CH$_2$—C(O)—O—(C$_2$H$_4$O)$_{14}$—C(O)—CH$_2$—CH$_2$—NEt$_2$,
—CH$_2$—CH$_2$—C(O)—O—(C$_2$H$_4$O)$_{14}$—C(O)—CH$_2$—CH$_2$—N(CH$_2$CH$_2$OH)$_2$,
—CH$_2$—CH$_2$—C(O)—O—(C$_2$H$_4$O)$_{14}$—C(O)CH$_3$,
—CH$_2$—CH$_2$—C(O)—O—(C$_2$H$_4$O)$_{35}$—H,
—CH$_2$—CH$_2$—C(O)—O—(C$_2$H$_4$O)$_{35}$—CH$_3$,
—CH$_2$—CH$_2$—C(O)—O—(C$_2$H$_4$O)$_{35}$—C(O)—CH=CH$_2$,
—CH$_2$—CH$_2$—C(O)—O—(C$_2$H$_4$O)$_{35}$—C(O)—CH$_2$—CH$_2$—NEt$_2$,
—CH$_2$—CH$_2$—C(O)—O—(C$_2$H$_4$O)$_{35}$—C(O)—CH$_2$—CH$_2$—N(CH$_2$CH$_2$OH)$_2$,
—CH$_2$—CH$_2$—C(O)—O—(C$_2$H$_4$O)$_{35}$—C(O)CH$_3$,
—CH$_2$—CH$_2$—C(O)—O—(C$_3$H$_6$O)$_6$—H,
—CH$_2$—CH$_2$—C(O)—O—(C$_3$H$_6$O)$_6$—CH$_3$,
—CH$_2$—CH$_2$—C(O)—O—(C$_3$H$_6$O)$_6$—C(O)—CH=CH$_2$,
—CH$_2$—CH$_2$—C(O)—O—(C$_3$H$_6$O)$_6$—C(O)—CH$_2$—CH$_2$—NEt$_2$,
—CH$_2$—CH$_2$—C(O)—O—(C$_3$H$_6$O)$_6$—C(O)—CH$_2$—CH$_2$—N(CH$_2$CH$_2$OH)$_2$,
—CH$_2$—CH$_2$—C(O)—O—(C$_3$H$_6$O)$_6$—C(O)CH$_3$,
—CH$_2$—CH$_2$—C(O)—O—(C$_3$H$_6$O)$_{12}$—H,
—CH$_2$—CH$_2$—C(O)—O—(C$_3$H$_6$O)$_{12}$—CH$_3$,
—CH$_2$—CH$_2$—C(O)—O—(C$_3$H$_6$O)$_{12}$—C(O)—CH=CH$_2$,
—CH$_2$—CH$_2$—C(O)—O—(C$_3$H$_6$O)$_{12}$—C(O)—CH$_2$—CH$_2$—NEt$_2$,
—CH$_2$—CH$_2$—C(O)—O—(C$_3$H$_6$O)$_{12}$—C(O)—CH$_2$—CH$_2$—N(CH$_2$CH$_2$OH)$_2$,
—CH$_2$—CH$_2$—C(O)—O—(C$_3$H$_6$O)$_{12}$—C(O)CH$_3$,
—CH$_2$—CH$_2$—C(O)—O—(C$_3$H$_6$O)$_{35}$—H,
—CH$_2$—CH$_2$—C(O)—O—(C$_3$H$_6$O)$_{35}$—CH$_3$,
—CH$_2$—CH$_2$—C(O)—O—(C$_3$H$_6$O)$_{35}$—C(O)—CH=CH$_2$,
—CH$_2$—CH$_2$—C(O)—O—(C$_3$H$_6$O)$_{35}$—C(O)—CH$_2$—CH$_2$—NEt$_2$,
—CH$_2$—CH$_2$—C(O)—O—(C$_3$H$_6$O)$_{35}$—C(O)—CH$_2$—CH$_2$—N(CH$_2$CH$_2$OH)$_2$,
—CH$_2$—CH$_2$—C(O)—O—(C$_3$H$_6$O)$_{35}$—C(O)CH$_3$,
—CH$_2$—CH$_2$—C(O)—O—(C$_3$H$_6$O)$_5$—(C$_2$H$_4$O)$_5$—H,
—CH$_2$—CH$_2$—C(O)—O—(C$_3$H$_6$O)$_5$—(C$_2$H$_4$O)$_5$—CH$_3$,
—CH$_2$—CH$_2$—C(O)—O—(C$_3$H$_6$O)$_5$—(C$_2$H$_4$O)$_5$C(O)—CH=CH$_2$,
—CH$_2$—CH$_2$—C(O)—O—(C$_3$H$_6$O)$_5$—(C$_2$H$_4$O)$_5$C(O)—CH$_2$—CH$_2$—NEt$_2$,
—CH$_2$—CH$_2$—C(O)—O—(C$_3$H$_6$O)$_5$—(C$_2$H$_4$O)$_5$C(O)—CH$_2$—CH$_2$—N(CH$_2$CH$_2$OH)$_2$,
—CH$_2$—CH$_2$—C(O)—O—(C$_3$H$_6$O)$_5$—(C$_2$H$_4$O)$_5$—C(O)CH$_3$,
—CH$_2$—CH$_2$—C(O)—O—(C$_3$H$_6$O)$_{10}$—(C$_2$H$_4$O)$_{10}$—H,
—CH$_2$—CH$_2$—C(O)—O—(C$_3$H$_6$O)$_{10}$—(C$_2$H$_4$O)$_{10}$—CH$_3$,
—CH$_2$—CH$_2$—C(O)—O—(C$_3$H$_6$O)$_{10}$—(C$_2$H$_4$O)$_{10}$C(O)—CH=CH$_2$,
—CH$_2$—CH$_2$—C(O)—O—(C$_3$H$_6$O)$_{10}$—(C$_2$H$_4$O)$_{10}$C(O)—CH$_2$—CH$_2$—NEt$_2$,
—CH$_2$—CH$_2$—C(O)—O—(C$_3$H$_6$O)$_{10}$—(C$_2$H$_4$O)$_{10}$C(O)—CH$_2$—CH$_2$—N(CH$_2$CH$_2$OH)$_2$,
—CH$_2$—CH$_2$—C(O)—O—(C$_3$H$_6$O)$_{10}$—(C$_2$H$_4$O)$_{10}$C(O)CH$_3$,
—CH$_2$—CH(OH)—CH$_2$—O—(C$_2$H$_4$O)$_4$—C$_4$H$_9$,
—CH$_2$—CH(OH)—CH$_2$—O—(C$_2$H$_4$O)$_{11}$—C$_4$H$_9$,
—CH$_2$—CH(OH)—CH$_2$—O—(C$_2$H$_4$O)$_{20}$—C$_4$H$_9$,
—CH$_2$—CH(OH)—CH$_2$—O—(C$_2$H$_4$O)$_{22}$(C$_3$H$_6$O)$_{19}$—C$_4$H$_9$,
—CH$_2$—CH(OH)—CH$_2$—O—(C$_2$H$_4$O)$_4$—C$_3$H$_5$O,
—CH$_2$—CH(OH)—CH$_2$—O—(C$_2$H$_4$O)$_{11}$—C$_3$H$_5$O,
—CH$_2$—CH(OH)—CH$_2$—O—(C$_2$H$_4$O)$_{20}$—C$_3$H$_5$O, —CH$_2$—CH(OH)—CH$_2$—O—(C$_2$H$_4$O)$_{22}$(C$_3$H$_6$O)$_{19}$—C$_3$H$_5$O,
—CH$_2$—CH(OH)—CH$_2$—O—(C$_2$H$_4$O)$_4$—CH$_2$—CH(OH)—CH$_2$—OH,
—CH$_2$—CH(OH)—CH$_2$—O—(C$_2$H$_4$O)$_{11}$—CH$_2$—CH(OH)—CH$_2$—OH,
—CH$_2$—CH(OH)—CH$_2$—O—(C$_2$H$_4$O)$_{20}$—CH$_2$—CH(OH)—CH$_2$—OH,
—CH$_2$—CH(OH)—CH$_2$—O—(C$_2$H$_4$O)$_{22}$(C$_3$H$_6$O)$_{19}$—CH$_2$—CH(OH)—CH$_2$—OH,
—CH$_2$—CH(OH)—CH$_2$—O—(C$_2$H$_4$O)$_4$—CH$_2$—CH(OH)—CH$_2$—NEt$_2$,
—CH$_2$—CH(OH)—CH$_2$—O—(C$_2$H$_4$O)$_{11}$—CH$_2$—CH(OH)—CH$_2$—NEt$_2$,
—CH$_2$—CH(OH)—CH$_2$—O—(C$_2$H$_4$O)$_{20}$—CH$_2$—CH(OH)—CH$_2$—NEt$_2$,
—CH$_2$—CH(OH)—CH$_2$—O—(C$_2$H$_4$O)$_{22}$(C$_3$H$_6$O)$_{19}$—CH$_2$—CH(OH)—CH$_2$—NEt$_2$,
—CH$_2$—CH(OH)—CH$_2$—O—(C$_2$H$_4$O)$_4$—CH$_2$—CH(OH)—CH$_2$—N(CH$_2$CH$_2$OH)$_2$,
—CH$_2$—CH(OH)—CH$_2$—O—(C$_2$H$_4$O)$_{11}$—CH$_2$—CH(OH)—CH$_2$—N(CH$_2$CH$_2$OH)$_2$,
—CH$_2$—CH(OH)—CH$_2$—O—(C$_2$H$_4$O)$_{20}$—CH$_2$—CH(OH)—CH$_2$—N(CH$_2$CH$_2$OH)$_2$, and
—CH$_2$—CH(OH)—CH$_2$—O—(C$_2$H$_4$O)$_{22}$(C$_3$H$_6$O)$_{19}$—CH$_2$—CH(OH)—CH$_2$—N(CH$_2$CH$_2$OH)$_2$, where Me is methyl and Et is ethyl.
Examples of J include
—CH$_2$—CH$_2$—C(O)—O—(C$_2$H$_4$O)$_6$—C(O)—CH$_2$—CH$_2$—,
—CH$_2$—CH$_2$—C(O)—O—(C$_2$H$_4$O)$_{14}$—C(O)—CH$_2$—CH$_2$—,
—CH$_2$—CH$_2$—C(O)—O—(C$_2$H$_4$O)$_{35}$—C(O)—CH$_2$—CH$_2$—,
—CH$_2$—CH$_2$—C(O)—O—(C$_3$H$_6$O)$_6$—C(O)—CH$_2$—CH$_2$—,
—CH$_2$—CH$_2$—C(O)—O—(C$_3$H$_6$O)$_{12}$—C(O)—CH$_2$—CH$_2$—,
—CH$_2$—CH$_2$—C(O)—O—(C$_3$H$_6$O)$_{35}$—C(O)—CH$_2$—CH$_2$—,
—CH$_2$—CH$_2$—C(O)—O—(C$_3$H$_6$O)$_5$—(C$_2$H$_4$O)$_5$—C(O)—CH$_2$—CH$_2$—,
—CH$_2$—CH$_2$—C(O)—O—(C$_3$H$_6$O)$_{10}$—(C$_2$H$_4$O)$_{10}$C(O)—CH$_2$—CH$_2$—,
—CH$_2$—CH$_2$—C(O)—O—(C$_3$H$_6$O)$_5$—(C$_2$H$_4$O)$_{15}$—C(O)—CH$_2$—CH$_2$—,
—CH$_2$—CH$_2$—C(O)—O—(C$_3$H$_6$O)$_{20}$—(C$_2$H$_4$O)$_{20}$—C(O)—CH$_2$—CH$_2$—,
—CH$_2$—CH$_2$—C(O)—NH—(C$_3$H$_6$O)$_3$—C$_3$H$_6$—NH—C(O)—CH$_2$—CH$_2$—,
—CH$_2$—CH$_2$—C(O)—NH—(C$_3$H$_6$O)$_6$—C$_3$H$_6$—NH—C(O)—CH$_2$—CH$_2$—,
—CH$_2$—CH$_2$—C(O)—NH—(C$_3$H$_6$O)$_{33}$—C$_3$H$_6$—NH—C(O)—CH$_2$—CH$_2$—,
—CH$_2$—CH$_2$—C(O)—NH—(C$_3$H$_6$O)$_{68}$—C$_3$H$_6$—NH—C(O)—CH$_2$—CH$_2$—,
—CH$_2$—CH$_2$—C(O)—NH—C$_3$H$_6$O—(C$_2$H$_4$O)$_2$—C$_3$H$_6$—NH—C(O)—CH$_2$—CH$_2$—,
—CH$_2$—CH$_2$—C(O)—NH—(C$_3$H$_6$O)$_2$—(C$_2$H$_4$O)$_9$—C$_3$H$_6$O—C$_3$H$_6$—NH—C(O)—CH$_2$—CH$_2$—,
—CH$_2$—CH$_2$—C(O)—NH—(C$_3$H$_6$O)$_3$—(C$_2$H$_4$O)$_{39}$—(C$_3$H$_6$O)$_2$—C$_3$H$_6$—NH—C(O)—CH$_2$—CH$_2$—,
—CH$_2$—CH(OH)—CH$_2$—O—(C$_2$H$_4$O)$_4$—CH$_2$—CH(OH)—CH$_2$—,
—CH$_2$—CH(OH)—CH$_2$—O—(C$_2$H$_4$O)$_{11}$—CH$_2$—CH(OH)—CH$_2$—,
—CH$_2$—CH(OH)—CH$_2$—O—(C$_2$H$_4$O)$_{20}$—CH$_2$—CH(OH)—CH$_2$—,
—CH$_2$—CH(OH)—CH$_2$—O—(C$_2$H$_4$O)$_{22}$(C$_3$H$_6$O)$_{19}$—CH$_2$—CH(OH)—CH$_2$—.

Examples of X$^-$ anions which are suitable according to the invention include chloride, bromide, hydrogensulfate, acetate, and sulfate ions and organic sulfonate ions, such as trifluoromethanesulfonate ion or p-toluenesulfonate ion. This list is exemplary and not limiting.

The invention further provides a process for preparing copolymers (Q) of the above general formula (I), which comprises reacting organosilicon compounds or mixtures thereof that are selected from compounds of the general formulae (XI), (XII), (XIII), (XIV) and (XV)

$$H-NR^1-(R-NHR^1)_g-R-(SiR^6_2O)_l-SiR^6_2-R(-NHR^1-R)_g-NR^1-H \quad (XI),$$

$$H-NR^1-(R-NHR^1)_g-R-(SiR^6_2O)_l-\{SiR^6[-R(-NHR^1-R)_g-NHR^1]-O\}_m-R(-NHR^1-R)_g-NR^1-H \quad (XII),$$

$$R^6_3SiO-(SiR^6_2O)_l-\{SiR^6[-R(-NHR^1-R)_g-NHR^1]-O\}_m-SiR^6_3 \quad (XIII),$$

$$MeO-SiR^6_2O-(SiR^6_2O)_l-\{SiR^6[-R(-NHR^1-R)_g-NHR^1]-O\}_m-SiR^6_2-OMe \quad (XIV),$$

$$H-NR^1-(R-NHR^1)_g-R-(SiR^6_2O)_l-SiR^6_2-R^8 \quad (XV),$$

with polyethers which are selected from compounds of the general formulae (XVI) and (XVII)

$$CH_2=CH-C(O)-G-(R^2-G)_h-[CH_2CH_2O]_i-[C_3H_6O]_j-[(CH_2)_4O]_k-(R^2-G)_h-R^5 \quad (XVI),$$

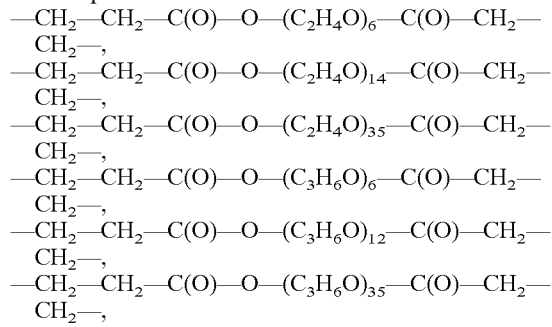

and organic compounds which are selected from compounds of the general formulae (XVIII) and (XIX)

where Me is methyl and R$^1$, R$^2$, R$^3$, R$^5$, R$^6$, G, X, g, h, i, j, k, l and m are each as defined above.

The process can be carried out in bulk, solution or emulsion, stepwise or as a one-pot process. The organosilicon compounds used are known and commercially available.

The cationic quat group is introduced in a different manner in the present process than is customary according to the prior art. The present process utilizes an aqueous reagent. Aqueous systems are inherently incompatible with hydrophobic siloxanes; modification of silicone oils using aqueous reagents is therefore customarily possible only with difficulties and to a poor yield. The present process, however, achieves excellent yields.

Examples of organosilicon compounds of the general formula (XI) which may be employed include
$H_2N$—$CH_2$—$SiMe_2O$—$SiMe_2$—$CH_2$—$NH_2$,
$H_2N$—$CH_2$—$SiMe_2O$—$(SiMe_2O)_6$—$SiMe_2$—$CH_2$—$NH_2$,
$H_2N$—$CH_2$—$SiMe_2O$—$(SiMe_2O)_{11}$—$SiMe_2$—$CH_2$—$NH_2$,
$H_2N$—$CH_2$—$SiMe_2O$—$(SiMe_2O)_{98}$—$SiMe_2$—$CH_2$—$NH_2$,
$H_2N$—$CH_2$—$SiMe_2O$—$(SiMe_2O)_{150}$—$SiMe_2$—$CH_2$—$NH_2$,
$H_2N$—$(CH_2)_3$—$SiMe_2O$—$SiMe_2$—$(CH_2)_3$—$NH_2$,
$H_2N$—$(CH_2)_3$—$SiMe_2O$—$(SiMe_2O)_6$—$SiMe_2$—$(CH_2)_3$—$NH_2$,
$H_2N$—$(CH_2)_3$—$SiMe_2O$—$(SiMe_2O)_{11}$—$SiMe_2$—$(CH_2)_3$—$NH_2$,
$H_2N$—$(CH_2)_3$—$SiMe_2O$—$(SiMe_2O)_{98}$—$SiMe_2$—$(CH_2)_3$—$NH_2$,
$H_2N$—$(CH_2)_3$—$SiMe_2O$—$(SiMe_2O)_{200}$—$SiMe_2$—$(CH_2)_3$—$NH_2$,
$H_2N$—$(CH_2)_2$—$NH$—$(CH_2)_3$—$SiMe_2O$—$SiMe_2$—$(CH_2)_3$—$NH$—$(CH_2)_2$—$NH_2$,
$H_2N$—$(CH_2)_2$—$NH$—$(CH_2)_3$—$SiMe_2O$—$(SiMe_2O)_6$—$SiMe_2$—$(CH_2)_3$—$NH$—$(CH_2)_2$—$NH_2$,
$H_2N$—$(CH_2)_2$—$NH$—$(CH_2)_3$—$SiMe_2O$—$(SiMe_2O)_{11}$—$SiMe_2$—$(CH_2)_3$—$NH$—$(CH_2)_2$—$NH_2$, and
$H_2N$—$(CH_2)_2$—$NH$—$(CH_2)_3$—$SiMe_2O$—$(SiMe_2O)_{55}$—$SiMe_2$—$(CH_2)_3$—$NH$—$(CH_2)_2$—$NH_2$—

Examples of organosilicon compounds of the general formula (XII) which may be employed include
$H_2N$—$(CH_2)_3$-$SiMe_2O$—$\{SiMe[(CH_2)_3$—$NH_2]O\}$—$SiMe_2$—$(CH_2)_3$—$NH_2$,
$H_2N$—$(CH_2)_3$—$SiMe_2O$—$(SiMe_2O)_{25}$—$\{SiMe[(CH_2)_3$—$NH_2]O\}_5$—$SiMe_2$—$(CH_2)_3$—$NH_2$,
$H_2N$—$(CH_2)_3$—$SiMe_2O$—$(SiMe_2O)_{50}$—$\{SiMe[(CH_2)_3$—$NH_2]O\}_3$—$SiMe_2$—$(CH_2)_3$—$NH_2$, and
$H_2N$—$(CH_2)_3$—$SiMe_2O$—$(SiMe_2O)_{70}$—$\{SiMe[(CH_2)_3$—$NH_2]O\}_1$—$SiMe_2$—$(CH_2)_3$—$NH_2$.

Examples of organosilicon compounds of the general formula (XIII) which may be employed include
$Me_3SiO$—$(SiMe_2O)_{25}$—$\{SiMe[(CH_2)_3$—$NH_2]O\}SiMe_3$,
$Me_3SiO$—$(SiMe_2O)_{45}$—$\{SiMe[(CH_2)_3$—$NH_2]O\}_5SiMe_3$,
$Me_3SiO$—$(SiMe_2O)_{100}$—$\{SiMe[(CH_2)_3$—$NH_2]O\}_5SiMe_3$,
$Me_3SiO$—$(SiMe_2O)_{130}$—$\{SiMe[(CH_2)_3$—$NH_2]O\}_1SiMe_3$,
$Me_3SiO$—$(SiMe_2O)_{105}\{SiMe[(CH_2)_3$—$NH$—$(CH_2)_2$—$NH_2]O\}_{20}$—$SiMe_3$,
$Me_3SiO$—$(SiMe_2O)_{195}(SiMe[(CH_2)_3$—$NH$—$(CH_2)_2$—$NH_2]O)_{15}$—$SiMe_3$,
$Me_3SiO$—$(SiMe_2O)_{230}(SiMe[(CH_2)_3$—$NH$—$(CH_2)_2$—$NH_2]O)_6$—$SiMe_3$,
$Me_3SiO$—$(SiMe_2O)_{108}(SiMe[(CH_2)_3$—$NH$—$(CH_2)_2$—$NH_2]O)_2$—$SiMe_3$, and
$Me_3SiO$—$(SiMe_2O)_{139}(SiMe[(CH_2)_3$—$NH$—$(CH_2)_2$—$NH_2]O)_1$—$SiMe_3$.

Examples of organosilicon compounds of the general formula (XIV) which may be employed include
$Me_3SiO$—$(SiMe_2O)_{25}$—$\{SiMe[(CH_2)_3$—$NH_2]O\}_5SiMe_3$,
$Me_3SiO$—$(SiMe_2O)_{45}$—$\{SiMe[(CH_2)_3$—$NH_2]O\}_5SiMe_3$,
$Me_3SiO$—$(SiMe_2O)_{100}$—$\{SiMe[(CH_2)_3$—$NH_2]O\}_5SiMe_3$,
$Me_3SiO$—$(SiMe_2O)_{130}$—$\{SiMe[(CH_2)_3$—$NH_2]O\}_1SiMe_3$,
$MeOSiMe_2O$—$(SiMe_2O)_{40}\{SiMe[(CH_2)_3$—$NH$—$(CH_2)_2$—$NH_2]O\}_1$—$SiMe_2OMe$,
$MeOSiMe_2O$—$(SiMe_2O)_{70}\{SiMe[(CH_2)_3$—$NH$—$(CH_2)_2$—$NH_2]O\}_1$—$SiMe_2OMe$,
$MeOSiMe_2O$—$(SiMe_2O)_{200}\{SiMe[(CH_2)_3$—$NH$—$(CH_2)_2$—$NH_2]O\}_1$—$SiMe_2OMe$.

Examples of employed organosilicon compounds of the general formula (XV) are
$H_2N$—$CH_2$—$(SiMe_2O)_{13}$—$SiMe_2$—$OCH_3$,
$H_2N$—$CH_2$—$(SiMe_2O)_{14}$—$SiMe_2$—$OC_2H_4$,
$H_2N$—$CH_2$—$(SiMe_2O)_{44}$—$SiMe_2$—$OC_3H_7$,
$H_2N$—$CH_2$—$(SiMe_2O)_{22}$—$SiMe_2$—$OC_4H_9$,
$H_2N$—$CH_2$—$(SiMe_2O)_{35}$—$SiMe_2$—$OC_4H_9$.
$H_2N$—$(CH_2)_3$—$(SiMe_2O)_9$—$SiMe_3$,
$H_2N$—$(CH_2)_3$—$(SiMe_2O)_{59}$—$SiMe_3$,
$H_2N$—$(CH_2)_3$—$(SiMe_2O)_{99}$—$SiMe_3$,
$H_2N$—$(CH_2)_3$—$(SiMe_2O)_{13}$—$SiMe_2$—$OCH_3$,
$H_2N$—$(CH_2)_3$—$(SiMe_2O)_{14}$—$SiMe_2$—$OC_2H_4$,
$H_2N$—$(CH_2)_3$—$(SiMe_2O)_{44}$—$SiMe_2$—$OC_3H_7$,
$H_2N$—$(CH_2)_3$—$(SiMe_2O)_{22}$—$SiMe_2$—$OC_4H_9$,
$H_2N$—$(CH_2)_3$—$(SiMe_2O)_{35}$—$SiMe_2$—$OC_4H_9$.
$H_2N$—$(CH_2)_2$—$NH$—$(CH_2)_3$—$(SiMe_2O)_7$—$SiMe_3$,
$H_2N$—$(CH_2)_2$—$NH$—$(CH_2)_3$—$(SiMe_2O)_{12}$—$SiMe_3$, with organosilicon compounds of the general formulae (XI), (XII), (XIII) and (XV) being preferred, especially organosilicon compounds of the general formulae (XI), (XIII) and (XV).

Examples of employed polyethers of the general formulae (XVI) and (XVII), which are likewise commercially available (for example from Cray Valley, Siber Hegner AG, NOF Corp.) or are preparable by methods known to one skilled in the art, are
$CH_2$=$CH$—$C(O)$—$O$—$(C_2H_4O)_6$—$H$,
$CH_2$=$CH$—$C(O)$—$O$—$(C_2H_4O)_{14}$—$H$,
$CH_2$=$CH$—$C(O)$—$O$—$(C_2H_4O)_{35}$—$H$,
$CH_2$=$CH$—$C(O)$—$O$—$(C_3H_6O)_6$—$H$,
$CH_2$=$CH$—$C(O)$—$O$—$(C_3H_6O)_{12}$—$H$,
$CH_2$=$CH$—$C(O)$—$O$—$(C_3H_6O)_{35}$—$H$,
$CH_2$=$CH$—$C(O)$—$O$—$(C_2H_4O)_3$—$(C_3H_6O)_3$—$H$,
$CH_2$=$CH$—$C(O)$—$O$—$(C_2H_4O)_5$—$(C_3H_6O)_5$—$H$,
$CH_2$=$CH$—$C(O)$—$O$—$(C_2H_4O)_{10}$—$(C_3H_6O)_{10}$—$H$,
$CH_2$=$CH$—$C(O)$—$O$—$(C_2H_4O)_6$—$CH_3$,
$CH_2$=$CH$—$C(O)$—$O$—$(C_2H_4O)_{16}$—$CH_3$,
$CH_2$=$CH$—$C(O)$—$O$—$(C_2H_4O)_{24}$—$CH_3$,
$CH_2$=$CH$—$C(O)$—$O$—$(C_2H_4O)_{25}$—$CH_3$,
$CH_2$=$CH$—$C(O)$—$O$—$(C_3H_6O)_6$—$CH_3$,
$CH_2$=$CH$—$C(O)$—$O$—$(C_3H_6O)_{12}$—$CH_3$,
$CH_2$=$CH$—$C(O)$—$O$—$(C_3H_6O)_{35}$—$CH_3$,
$CH_2$=$CH$—$C(O)$—$O$—$(C_2H_4O)_3$—$(C_3H_6O)_3$—$CH_3$,
$CH_2$=$CH$—$C(O)$—$O$—$(C_2H_4O)_5$—$(C_3H_6O)_5$—$CH_3$,
$CH_2$=$CH$—$C(O)$—$O$—$(C_2H_4O)_{10}$—$(C_3H_6O)_{10}$—$CH_3$,
$CH_2$=$CH$—$C(O)$—$O$—$(C_2H_4O)_3$—$C(O)$—$CH$=$CH_2$,
$CH_2$=$CH$—$C(O)$—$O$—$(C_2H_4O)_6$—$C(O)$—$CH$=$CH_2$,
$CH_2$=$CH$—$C(O)$—$O$—$(C_2H_4O)_{14}$—$C(O)$—$CH$=$CH_2$,
$CH_2$=$CH$—$C(O)$—$O$—$(C_2H_4O)_{35}$—$C(O)$—$CH$=$CH_2$,
$CH_2$=$CH$—$C(O)$—$O$—$(C_3H_6O)_3$—$C(O)$—$CH$=$CH_2$,
$CH_2$=$CH$—$C(O)$—$O$—$(C_3H_6O)_6$—$C(O)$—$CH$=$CH_2$,
$CH_2$=$CH$—$C(O)$—$O$—$(C_3H_6O)_{12}$—$C(O)$—$CH$=$CH_2$,
$CH_2$=$CH$—$C(O)$—$O$—$(C_3H_6O)_{35}$—$C(O)$—$CH$=$CH_2$,
$CH_2$=$CH$—$C(O)$—$O$—$(C_2H_4O)_3$—$(C_3H_6O)_3$—$C(O)$—$CH$=$CH_2$,
$CH_2$=$CH$—$C(O)$—$O$—$(C_2H_4O)_5$—$(C_3H_6O)_5$—$C(O)$—$CH$=$CH_2$, $CH_2=CH-C(O)-O-(C_2H_4O)_{10}-(C_3H_6O)_{10}-C(O)-CH=CH_2,$

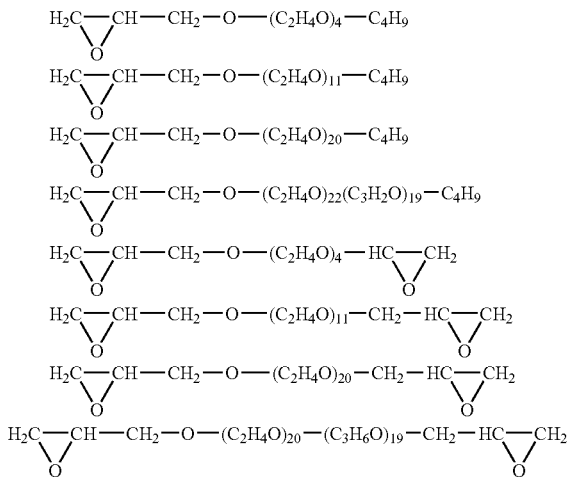

Examples of organic compounds of the general formulae (XVIII) and (XIX), which may be employed and which are likewise commercially available (for example from Degussa AG), include

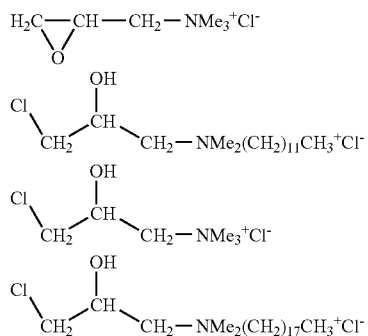

It is preferable to use at least 0.001 mol, more preferably at least 0.1 mol, yet more preferably at least 0.5, and preferably at most 1.75 mol of polyether of the general formulae (XVI) and (XVII) and also preferably at least 0.001 mol, more preferably at least 0.1 mol, yet more preferably at least 0.5, and preferably at most 1.75 mol of organic compound of the general formulae (XVIII) and (XIX) in the process, per mole of amine group of the organosilicon compound of the general formulae (XI), (XII), (XIII), (XIV) and (XV).

When the process utilizes difunctional polyether compounds of the general formulae (XVI) and (XVII) and the fractions of polyether compound of the general formulae (XVI) and (XVII) and of the organic compound of the general formulae (XVIII) and (XIX) are chosen such that excess acrylate and epoxy radicals appear in the copolymers of the general formula (I), these reactive end groups may subsequently crosslink or be specifically crosslinked.

The products of the general formula (I) having reactive acrylate and epoxy end groups can be rendered stable in storage for several months against free-radical crosslinking in daylight by means of the customary free-radical inhibitors such as hydroquinone monomethyl ether or phenothiazine.

Stabilization against possible postcrosslinking due to primary or secondary amine groups which remain in the product with the acrylate or epoxy end groups can be achieved by amidating these amine groups with organic acid anhydrides or acyl chlorides, or by a Michael-type reaction to saturate the amine groups with monomeric acrylic ester compounds after the actual reaction has taken place. Remaining primary or secondary amine groups in the copolymers of the general formula (I) may in addition also be protonated, alkylated or quaternized; this also applies to tertiary amine groups. The process for preparing the copolymers of the general formula (I) may utilize compounds known from the literature which catalyze Michael-type reactions and epoxy ring opening reactions. Examples are Bronsted acids such as phosphoric acid, sulfuric acid, hydrochloric acid, glacial acetic acid, propionic acid and formic acid, or their aqueous solutions; Lewis acids such as lithium perchlorate, zinc tetrafluoroborate, iron(II) chloride and tin (IV) chloride, and Brønsted bases, for example sodium methoxide and alkali metal amides, and also ammonium chloride, tetraalkylammonium bromides and alkali metal iodides.

The process may additionally employ organic solvents, water, or mixtures thereof, the abovementioned polyethers of the general formulae (XVI) and (XVII) and also the reaction product itself also potentially serving as a solvent. Examples of organic solvents are toluene, xylene, THF, n-butyl acetate, isopropanol, butanol and dimethoxyethane. Organic solvent used is preferably removed again after the reaction or after follow-up reactions.

When the process is carried out in emulsion, emulsifiers or surface-active agents may correspondingly be present. Similarly, when the process is carried out in emulsion, the reaction product itself may by virtue of its surface-active properties be used as an emulsifier or coemulsifier.

The copolymers of the general formula (I) can be equilibrated with organopolysiloxanes selected from the group consisting of linear organopolysiloxanes having terminal triorganosiloxy groups, organopolysiloxanes having linear, terminal hydroxyl groups, cyclic organopolysiloxanes and interpolymers of diorganosiloxane and monoorganosiloxane units.

As linear organopolysiloxanes having terminal triorganosiloxy groups it is preferable to use those of the general formula (XX)

as linear organopolysiloxanes having terminal hydroxyl groups it is preferable to use those of the general formula (XXI)

as cyclic organopolysiloxanes it is preferable to use those of the general formula (XXII)

and as interpolymers it is preferable to use those composed of units of the general formulae (XXIII), (XXIV) and (XXV)

where q and r are each 0 or an integer from 1 to 1500, s is an integer from 3 to 12, and $R^6$ is as defined above.

The quantitative ratios of the organopolysiloxanes of the general formulae (XX) to (XXV) that are used in the optionally conducted equilibration and of the copolymers of the general formula (I) are merely determined by the fraction of polyether and/or quat groups which is desired in the copolymers produced in the optionally conducted equilibration and by the average chain length desired for the siloxane units.

The optionally conducted equilibration utilizes acidic catalysts, or preferably, basic catalysts, to further the equilibration. Examples of preferable acidic catalysts include sulfuric acid, phosphoric acid, trifluoromethanesulfonic acid, phosphorus nitride chlorides and acidic catalysts which are solid under the reaction conditions, such as acid-activated bleaching earth, acidic zeolites, sulfonated carbon and sulfonated styrene-divinylbenzene interpolymer, with phosphorus nitride chlorides being preferred as acidic catalysts. Acidic catalysts are preferably used in amounts from 5 to 1000 weight ppm (parts per million), more preferably 50 to 200 weight ppm, all based on the total weight of the organosilicon compounds used. Examples of basic catalysts include benzyltrimethylammonium hydroxide, tetramethylammonium hydroxide, alkali metal hydroxides, alkaline earth metal hydroxides in methanolic solution, phosphonium hydroxides, and silanolates. Preference is given to ammonium hydroxides, which are used in amounts from 50 to 10,000 weight ppm more preferably 500 to 2000 weight ppm, all based on the total weight of the organosilicon compounds used.

The optionally conducted equilibration is preferably conducted at 80 to 150° C. and at the pressure of the surrounding atmosphere, i.e., between 900 and 1100 hPa. If desired, however, higher or lower pressures can be employed as well. The equilibrating can be conducted in water-immiscible solvents, such as toluene. When solvents are used, the amounts employed are preferably 5 to 20 weight percent, based on the total weight of the particular organosilicon compounds used. The catalyst can be rendered inactive before the as-equilibrated mixture is worked up.

Advantages of the process for preparing the copolymers of the general formula (I) are the simple implementation in the form of a one-pot synthesis and the use of starting materials which are simple and commercially available in a large variety. The process has the further advantage that, first, the properties of the copolymers are easily varied through the choice of reactants, and second, to a certain extent, the stoichiometry of the reactants can be used with otherwise virtually unchanged reaction parameters to vary not only the viscosity but to simply vary also the hydrophilicity, the amine number, and the nature of the end groups of the products, as well as the ratio of the siloxane to polyether and/or quat units.

The copolymers (Q) of the general formula (I) are notable for transparency, low discoloration, hydrolysis resistance and transition metal absence. Owing to their cationogenicity, which is due to the number of quaternary amino groups in the molecule, the copolymers of the invention possess very good adhesion to substrates such as textiles or paper and are notable for their hydrophilicity, which is comparatively high for organosilicon compounds.

The copolymers (Q) are therefore useful, for example, as ingredients of emulsions, in solution or in solvent-free compositions for the treatment of textile sheet materials, for example wovens, knits or nonwovens, textile fiber and yarn finishing and modification and also leather and paper treatment. Finishing or modifying with the appropriate copolymers (Q) can be used to confer desired properties such as for example a soft, supple hand, improved elasticity, antistatic properties, modified coefficients of friction, surface smoothness, luster, crease recovery, color fastnesses, durability to laundering, hydrophilicity, tear strength, reduced tendency to pill, easy care and soil release properties and also improved wear comfort. The effects achieved through finishing with the copolymers (Q) exhibit good to very good durability to washing and reconditioning operations, depending on the structure of the copolymer (Q), on the structure of the substrate and on the wash conditions. The finishing or modification of textile sheet materials, fibers, yarns, paper and leather with the copolymers (Q) can further be used to improve the industrial processability, for example the processing and manufacturing speed, and also the quality of the materials.

The textile sheet materials fibers and yarns may have been fabricated from mineral fibers, such as glass fibers or silicate fibers, natural fibers such as for example wool, silk or cotton, manufactured fibers, such as for example polyester or polyamide fibers, cellulose fibers, interpolymer fibers or metal fibers. Filament fibers or staple fibers composed of the substrates mentioned can likewise be used. It is further possible to use sheet materials composed of fiber blends, such as cotton/polyester, paper and also natural sheet materials such as leather.

The coating or finish can be applied in the knife coating process, dip (squeeze) process, extrusion process, spraying flocking or atomizing process, padding, exhaust or dip-whiz processes. Similarly, all varieties of roller coatings, such as gravure roll, kiss roll, or application via multiroll systems, and also printing, for example (rotary) screen printing, are possible. Finishing or coating can further be carried out by foam application and subsequent calendering, using a calender, including a hotmelt calender.

The copolymers (Q) can further be used as additives in coatings and paints. Additions of the copolymers (Q) to, for example, radiation- or addition-curing paints lead to a reduction in the surface roughness and thus to a reduction in the slip resistance of the paint. The copolymers (Q) can further serve as ingredients in cosmetic formulations, for example as conditioners in hair shampoos, and as building protectants. In addition, the copolymers (Q) constitute surface-active agents and can be used as detergents, surfactants, emulsifiers, defoamers and foam stabilizers.

All the above symbols in the above formulae each have their meanings independently of each other. The silicon atom is tetravalent in all the formulae. Where a hydrocarbyl group may be interrupted by a heteroatom or heteroatom-containing group, may be substituted, or may contain enumerated organic groups, these modifications of the hydrocarbyl group are not exclusive, and a given hydrocarbyl group may contain none, all, or any combination of these modifications, unless otherwise indicated.

EXAMPLES

In the examples which follow, all parts and percentages are by weight, unless otherwise stated. Also, unless otherwise stated, the examples are carried out at the pressure of the surrounding atmosphere, i.e., at about 1000 hPa, and at room temperature, i.e., at about 20° C. or at a temperature which results without additional heating and cooling when the reactants are added together at room temperature. All viscosities reported in the examples relate to a temperature of 25° C. AN is the amine number, the amine number being the number of ml of 1N HCl which is needed to neutralize 1 g of substance.

Example 1

250 g of a terminally aminopropyl-functional silicone oil (AN=0.18) are stirred at 50° C. for 12 h with 4.85 g of a 70% aqueous solution of 2,3-epoxypropyltrimethylammonium chloride (QUAB® 151, Degussa AG) in 4 g of i-propanol. Subsequently, 25.69 g of an α-acrylate- and ω-methoxy-functionalized oligoethylene glycol (MW=ca. 1142) in 250 g of i-propanol are added and stirred in under reflux conditions for 2 h. Removal of the solvent under reduced pressure leaves 279 g of a colorless tallowy solid (AN=0.16).

Example 2

250 g of a terminally aminopropyl-functional silicone oil (AN=0.26) are stirred at 50° C. for 12 h with 14.02 of a 70% aqueous solution of 2,3-epoxypropyltrimethylammonium chloride (QUAB® 151, Degussa AG) in 10 g of i-propanol. 143 g of an α-glycidoxy- and ω-butoxy-functionalized polyethylene glycol-polypropylene glycol copolymer (MW=ca. 2200; about 22 EO units and 19 PO units) in 250 g of i-propanol are added and stirred in under reflux conditions for a further 6 h. Removal of the solvent under reduced pressure leaves 302.5 g of a colorless solid (AN=0.21).

Example 3

250 g of a terminally aminopropyl-functional silicone oil (AN=0.56) are stirred at 50° C. for 12 h with 15.1 g of a 70% aqueous solution of 2,3-epoxypropyltrimethylammonium chloride (QUAB® 151, Degussa AG) in 10.6 g of i-propanol. Subsequently, 67 g of an α-glycidoxy- and ω-butoxy-functionalized polyethylene glycol (MW=ca. 319) in 250 g of i-propanol are added and stirred in under reflux conditions for a further 6 h. Removal of the solvent under reduced pressure leaves 327.5 g of a white waxy solid (AN=0.42).

Example 4

250 g of an a-aminopropyl- and w-i-butoxy-functional silicone oil (AN=0.5) are stirred at 50° C. for 12 h with 27 g of a 70% aqueous solution of 2,3-epoxypropyltrimethylammonium chloride (QUAB® 151, Degussa AG) in 19 g of i-propanol. Subsequently, 142.75 g of an α-acrylate- and 8,51-methoxy-functionalized oligoethylene glycol (MW=ca. 1142) in 250 g of i-propanol are added and stirred in under reflux conditions for 4 h. Removal of the solvent under reduced pressure leaves 412 g of a slightly yellowish solid (AN=0.30).

Example 5

250 g of an aminoethylaminopropyl-functionalized silicone oil having trimethylsilyl end groups (AN=0.25) are stirred at 50° C. for 12 h with 13.48 g of a 70% aqueous solution of 2,3-epoxypropyltrimethylammonium chloride (QUAB® 151, Degussa AG) in 9.5 g of i-propanol. Subsequently, 25.2 g of an α-acrylate- and ω-methoxy-functionalized oligoethylene glycol (MW=ca. 807) in 250 g of i-propanol are added and stirred in under reflux conditions for 3 h. Removal of the solvent under reduced pressure leaves 284.5 g of a slightly yellowish solid (AN=0.22).

Example 6

250 g of an aminoethylaminopropyl-functionalized silicone oil having trimethylsilyl end groups (AN=0.60) are stirred at 70° C. for 12 h with 64.13 g of an aqueous solution of 2,3-epoxypropyldimethyldodecylammonium chloride (QUAB® 342, Degussa AG) and 4.35 g of KOH in 100 g of ethanol. Subsequently, 75.8 g of an α-glycidoxy- and ω-butoxy-functionalized polyethylene glycol (MW=ca. 1010) and 150 g of i-propanol are added and stirred in under reflux conditions for a further 8 h. Removal of the solvent under reduced pressure leaves 351 g of a white waxy solid (AN=0.43).

Example 7

250 g of a terminally aminopropyl-functional silicone oil (AN=0.18) are stirred at 50° C. for 12 h with 9.7 g of a 70% aqueous solution of 2,3-epoxypropyltrimethylammonium chloride (QUAB® 151, Degussa AG) in 7 g of i-propanol. Subsequently, 12.45 g of an α,ω-diacrylate-functionalized oligoethylene glycol (MW=ca. 830) and 34.2 g of an a-acrylate- and w-methoxy-functionalized oligoethylene glycol (MW=ca. 1142) in 250 g of i-propanol are added and stirred in under reflux conditions for 4 h. Removal of the solvent under reduced pressure leaves 303 g of a slightly yellowish tallowy solid (AN=0.15).

Example 8

250 g of a terminally aminopropyl-functional silicone oil (AN=0.18) are stirred at 50° C. for 12 h with 9.7 g of a 70% aqueous solution of 2,3-epoxypropyltrimethylammonium chloride (QUAB® 151, Degussa AG) in 7 g of i-propanol. Subsequently, 38 g of an a,w-diacrylate-functionalized oligoethylene glycol (MW=ca. 1126) in 250 g of i-propanol are added and stirred in under reflux conditions for 2 h. Removal of the solvent under reduced pressure leaves 295 g of a slightly yellowish tallowy solid (AN=0.15).

Performance Examples

Padding Process:

A bleached, unfinished PES/CO 65/35 twill fabric having a basis weight of 200 g/m$^2$ was used. The reference used was a finish with a standard silicone softener emulsion (microemulsion of an amino-functional polydimethylsiloxane) and also fabric padded with water and dried.

The fabric was saturated with the respective liquor, squeezed off to 70% wet pickup on a two-bowl pad-mangle, tentered and dried in a Mathis laboratory tenter at 150° C. for 2 min. The fabric was then conditioned at 23° C. and a relative humidity of 50% for at least 12 hours.

Determination methods for the results of the performance examples:

A) Determination of Soft Hand (Hand Assessment)

Since the soft hand of textiles is greatly dependent on the subjective feel of the tester, only the boundary conditions can be standardized and not the assessment itself. To ensure reproducibility nonetheless, the finished samples were assessed and ranked in order with regard to their soft hand. To this end, 10 testers awarded 1 to n points to n tested samples, n points being awarded to the softest sample and 1 point to the least soft sample. The reported result is accordingly the average value of points scored by each sample.

B) Determination of Droplet Absorption Time

After finishing, the finished sample was conditioned at 23° C. and 50% relative humidity for eight hours before a droplet of deionized water was placed on the tensioned fabric surface from a height of 6 cm and the time taken for the droplet of water to be absorbed by the fabric was determined, 3 minutes being the longest time allowed. Five determinations were carried out and the results averaged.

Table 1 summarizes for some performance examples the results of the fabric finished by means of the padding process.

TABLE 1

| | Examples | | | | | | | | | |
|---|---|---|---|---|---|---|---|---|---|---|
| Emulsion of | 9 | 10 | 11 | 12 | 13 | 14 | 15 | 16 | C1 | C2 |
| Example 1 | 20 g/l | | | | | | | | | |
| Example 2 | | 20 g/l | | | | | | | | |
| Example 3 | | | 20 g/l | | | | | | | |
| Example 4 | | | | 20 g/l | | | | | | |
| Example 5 | | | | | 20 g/l | | | | | |
| Example 6 | | | | | | 20 g/l | | | | |
| Example 7 | | | | | | | 20 g/l | | | |
| Example 8 | | | | | | | | 20 g/l | | |
| Standard Si microemulsion | | | | | | | | | 20 g/l | |
| Glacial acetic acid | 0.5 g/l | 0.5 g/l | 0.5 g/l | 0.5 g/l | 0.5 g/l | 0.5 g/l | 0.5 g/l | 0.5 g/l | 0.5 g/l | 0.5 g/l |
| Droplet absorption time (seconds) | 16 | <1 | <1 | <1 | 130 | 54 | 8 | 13 | >180 | 108 |
| Hand | 7.1 | 2.1 | 3.6 | 1.9 | 6.3 | 3.8 | 7.9 | 8.7 | 3.6 | 0 |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A copolymer (Q) of the formula (I) which is water soluble or self-emulsifying, $$A\text{—}B\text{—}(D\text{—}B)_s\text{—}A \quad (I),$$

where

A is an $-R^1$ or $-OR^1$ radical or a monovalent radical of the formula (II),

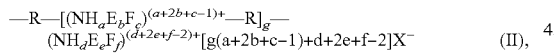

$R^1$ is a hydrogen atom or a monovalent hydrocarbyl radical having 1 to 100 carbon atoms optionally interrupted by and/or substituted by one or more of N, O, P, B, Si, or S, optionally containing one or more of $-C(O)-$, $-C(O)O-$, $-C(O)NR^9-$, $-NR^9-$, $-O-$, $-S-$, $=N-$, or $\equiv N$ units, and optionally substituted by one or more $-NR^9-$, $-OH$, or $-SH$ groups, R is a divalent hydrocarbyl radical having 1 to 50 carbon atoms optionally interrupted by and optionally substituted by one or more of N, O, P, B, Si, S and which optionally contains one or more $-C(O)-$, $-C(O)O-$, $-C(O)NR^9-$, $-NR^9-$, $-O-$, $-S-$, or $=N-$ units, $R^9$ is a hydrogen atom or a monovalent hydrocarbyl radical having 1 to 18 carbon atoms optionally interrupted by one or more of N, O, P, B, Si, S, and optionally substituted by one or more of $-OH$, or $-SH$ groups, a, b and c are integers from 0 to 2 subject to the condition that the sum of a+b+c is 1 or 2, d, e and f are integers from 0 to 3 subject to the condition that the sum of d+e+f is 2 or 3, g is an integer from 0 to 10, s is an integer >0 and less than 100, E is a radical of the formula (III)

$$-R^2-NR^3_3{}^+ \quad (III),$$

$R^2$ is a divalent hydrocarbyl radical having 1 to 10 carbon atoms optionally interrupted by and optionally substituted by one or more of N, O, P, B, Si, or S, and optionally containing one or more of $-C(O)-$, $-C(O)O-$, $-C(O)NR^9-$, $-NR^9-$, $-O-$, $-S-$, $=N$, or $\equiv N$ units, and optionally substituted by one or more of $-NR^9-$, $-OH$, or $-SH$ groups, $R^3$ is a monovalent hydrocarbyl radical having 1 to 20 carbon atoms optionally interrupted by and optionally substituted by one or more of N, O, P, B, Si, or S, optionally containing one or more of $-C(O)-$, $-C(O)O-$, $-C(O)NR^9-$, $-NR^9-$, $-O-$, $-S-$, $=N-$, or $\equiv N$ units, and substituted by one or more of $-NR^9-$, $-OH$, and/or $-SH$ groups, $X^-$ is an organic or inorganic anion, F is a radical of the formulae (IV) or (V)

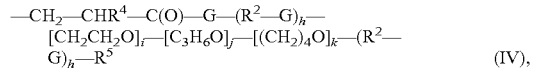
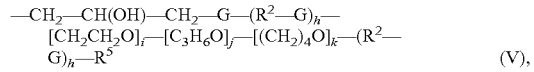

$R^4$ is a hydrogen atom or methyl radical, $R^5$ is a hydrogen atom, a monovalent branched or unbranched hydrocarbyl radical having 1 to 10 carbon atoms or a unit selected from the group consisting of $CH_2=CR^4-C(O)-$, $(R^1)_2N-CH_2-CHR^4-C(O)-$, $R^4-CH_2-C(O)-$, $HO-CH_2-CH(OH)-CH_2-$ and

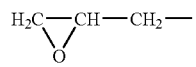

G is a divalent group $-O-$ or $-NR^9-$, h is 0 or 1, i, j and k are each an integer from 0 to 200, B is a divalent radical comprising one or more units which are selected from the formulae (VIa), (VIb), (VIc), (VId) and A $(SiR^6{}_2O_{2/2})_l$ (VIa), $(SiR^6R^7O_{2/2})_m$ (VIb), $(-SiR^6{}_2-)_{p+1}$ (VIc), $(SiO_{3/2})_p$ (VId), $R^6$ is a hydrogen atom, $-OR^1$, or a monovalent alkyl radical having 1 to 200 carbon atoms optionally substituted by one or more of halogen atoms, carboxyl groups, epoxy groups, hydroxyl groups or polyether groups, and optionally interrupted by one or more of the units $-C(O)-$, $-C(O)O-$, $-C(O)NR^9-$, $-NR^9-$, $-O-$, or $-S-$, $R^7$ is a monovalent radical of the formula (II), l and m are each an integer from 0 to 5000, p is an integer from 0 to 500, D is a divalent radical of the formula (VIII), $-\{[R-(NH_aE_bF_c)]-J-[(NH_aE_bF_c)-R]_n\}-^{[2n(a+2b+c)-4]+}[2n(a+2b+c)-4]X^-$ (VIII), n is an integer from 1 to 10, J is a divalent radical of the formulae (IX) or (X), $-CH_2-CHR^4-C(O)-G-(R^2-G)_h-$
$[CH_2CH_2O]_i-[C_3H_6O]_j-[(CH_2)_4O]_k-(R^2-$
$G)_h-C(O)-CHR^4-CH_2-$ (IX), $-CH_2-CH(OH)-CH_2-G-(R^2-G)_h-$
$[CH_2CH_2O]_i-[C_3H_6O]_j-[(CH_2)_4O]_k-(R^2-$
$G)_h-CH_2-CH(OH)-CH_2-$ (X), with the proviso that the copolymers of the formula (I) contain at least one E radical and one F radical.

2. The copolymer (Q) of claim 1 having an average molecular weight $M_n$ from 500 g/mol to 1,000,000 g/mol.

3. The copolymer (Q) of claim 1, wherein R is a $-(CH_2)-$, $-(CH_2)_2-$ or $-(CH_2)_3-$ radical.

4. The copolymer (Q) of claim 1, wherein $R^1$ is hydrogen, methyl, ethyl, propyl, cyclohexyl or acetyl.

5. The copolymer (Q) of claim 1, wherein $R^2$ is a linear or branched alkylene radical.

* * * * *